United States Patent [19]

Apple et al.

[11] Patent Number: 4,987,083
[45] Date of Patent: Jan. 22, 1991

[54] PHOTOMETRIC ANALYZER AND CONTROLLER FOR BEVERAGES

[76] Inventors: Glenn D. Apple, 808 Rockwood La., Newark, Del. 19713; Robert S. Saltzman, 6 Sorrel Dr., Surrey Park, Delaware, Del. 19803; Stewart W. Sennet, 913 Bradley Dr., Wilmington, Del. 19808

[21] Appl. No.: 195,608

[22] Filed: May 18, 1988

Related U.S. Application Data

[63] Continuation-in-part of Ser. No. 947,318, Dec. 29, 1986, abandoned.

[51] Int. Cl.$^5$ .............................................. G01N 35/08
[52] U.S. Cl. ....................................... 436/55; 436/53; 436/20; 436/24; 422/67; 422/81; 422/82; 426/477; 426/590; 141/105
[58] Field of Search ........................ 426/231, 477, 590; 422/67, 81, 82, 121; 436/52, 53, 20, 24, 55; 141/183, 100, 105

[56] References Cited

U.S. PATENT DOCUMENTS

| | | | |
|---|---|---|---|
| 3,158,163 | 11/1964 | Claudy | 436/55 |
| 3,283,644 | 11/1966 | Saltzman | 88/14 |
| 3,306,156 | 2/1967 | Glasser et al. | 88/14 |
| 3,608,779 | 9/1971 | Cornelius | 426/477 |
| 3,912,393 | 10/1975 | Hossom et al. | 356/36 |
| 4,114,635 | 9/1978 | Heckler, IV | 137/3 |
| 4,257,259 | 3/1981 | Ford | 73/61.1 C |
| 4,311,485 | 1/1982 | Saltzman | 23/230 R |
| 4,329,048 | 5/1982 | Capatini et al. | 356/73 |
| 4,329,149 | 5/1982 | Schoonover et al. | 23/230 R |
| 4,335,438 | 6/1982 | Smolen | 422/81 |
| 4,379,636 | 4/1983 | Yoshiba | 356/407 |
| 4,380,586 | 4/1983 | Saltzman | 436/121 |
| 4,403,861 | 9/1983 | Boisde et al. | 356/407 |
| 4,599,234 | 7/1986 | Wieland et al. | 426/590 |

FOREIGN PATENT DOCUMENTS 824047  4/1981  U.S.S.R. ................. 436/24

*Primary Examiner*—Robert J. Warden
*Assistant Examiner*—Lynn M. Kummert
*Attorney, Agent, or Firm*—Webb, Burden, Ziesenheim & Webb

[57] ABSTRACT

An improved process and apparatus for making carbonated beverages in which water is mixed with a syrup and the resulting mixture is carbonated and filled into containers in a filling line, the improvement is the following:

a sample of beverage is continuously removed before the beverage is filled into containers and then the sample is passed into a cell of a photometric analyzer and the concentration of syrup is photometrically measured which generates a signal; the signal is fed to a process controller which compares the signal to a signal stored in the controller having been generated by the photometric analyzer of an analysis of a sample of a standard beverage containing a predetermined level of syrup concentration and precisely determines the deviation of syrup concentration of the sample from the standard; a trim amount of water is added to the beverage to control the syrup concentration of the beverage to the concentration level of the standard; and the beverage is passed through a static-in-line mixer to provide thorough mixing of the beverage and then the beverage is filled into containers.

11 Claims, 2 Drawing Sheets

4,987,083

PHOTOMETRIC ANALYZER AND CONTROLLER FOR BEVERAGES

CROSS REFERENCE TO RELATED APPLICATIONS

This application is a continuation-in-part application of Serial No. 947,318 filed Dec. 29, 1986, now abandoned.

BACKGROUND OF THE INVENTION

This invention relates to an apparatus and process for analyzing and controlling the content of ingredients used in beverages.

In the preparation of carbonated beverages, a flavoring syrup is mixed with water and then the mixture is carbonated, usually chilled and then by using conventional filling equipment the resulting beverage is filled into containers such as bottles or cans. A critical component of the beverage is its syrup content. To provide a beverage that has a uniform taste and appearance, the syrup content must be held at a constant level. Also, significant quality improvement and/or cost savings can be realized if the correct syrup content is used.

The syrup content of the beverage can be monitored by analyzing the contents of a container after filling or removing a sample of beverage from the filling line and analyzing its syrup content and then if needed the ratio of syrup to water is adjusted to bring the syrup content of the beverage within a predetermine level. However, these methods are relatively slow and allow for a large number of containers to be filled before an adjustment of syrup content of the beverage can be made. An additional problem has presented itself with sugar-free beverages. In a conventional process, the syrup content of the beverage was determined by measuring the sugar content of the beverage which of course is not possible with a sugar-free beverage.

There is a need for a process and apparatus that will measure the syrup content of carbonated beverages in particular sugar-free beverages and make in line adjustments so that the syrup content of the beverage is adjusted to be within its desired level before it is filled into a container.

SUMMARY OF THE INVENTION

An improved process and apparatus for making carbonated beverages in which water is mixed with a syrup in a mixing vessel and the resulting mixture is passed into a carbonator and the beverage is carbonated and a flow stream of the resulting carbonated beverage is passed into a filling machine and filled into containers in a filling line, the improvement used therewith are the following steps:

a. continuously removing a sample of beverage from the flow stream after the beverage has been carbonated and before the beverage is filled into containers and then passing the sample of beverage into a cell of a photometric analyzer and photometrically measuring the concentration of syrup in the sample which generates a signal and returning the sample to the flow stream;

b. feeding the above signal to a process controller which compares the signal to a signal stored in the controller that had been generated by the photometric analyzer of an analysis of a sample of a standard beverage containing a predetermined level of syrup concentration and the process controller precisely determines the deviation of syrup concentration of the sample from the standard;

c. adding a trim amount of water to the flow stream of the beverage after the beverage has left the mixing vessel and has been carbonated to control the syrup concentration of the beverage to the concentration level of the standard wherein the process controller monitors and controls the trim amount of water being added;

d. passing the beverage through a static-in-line mixer to provide thorough mixing of the beverage.

DETAILED DESCRIPTION OF THE INVENTION

The improved process and apparatus of this invention make it possible to accurately control the syrup content of carbonated beverages. In particular, the syrup content of those carbonated beverages that use a sugar-free syrup can be precisely controlled which is very difficult or impossible with conventional equipment.

Figure 1:
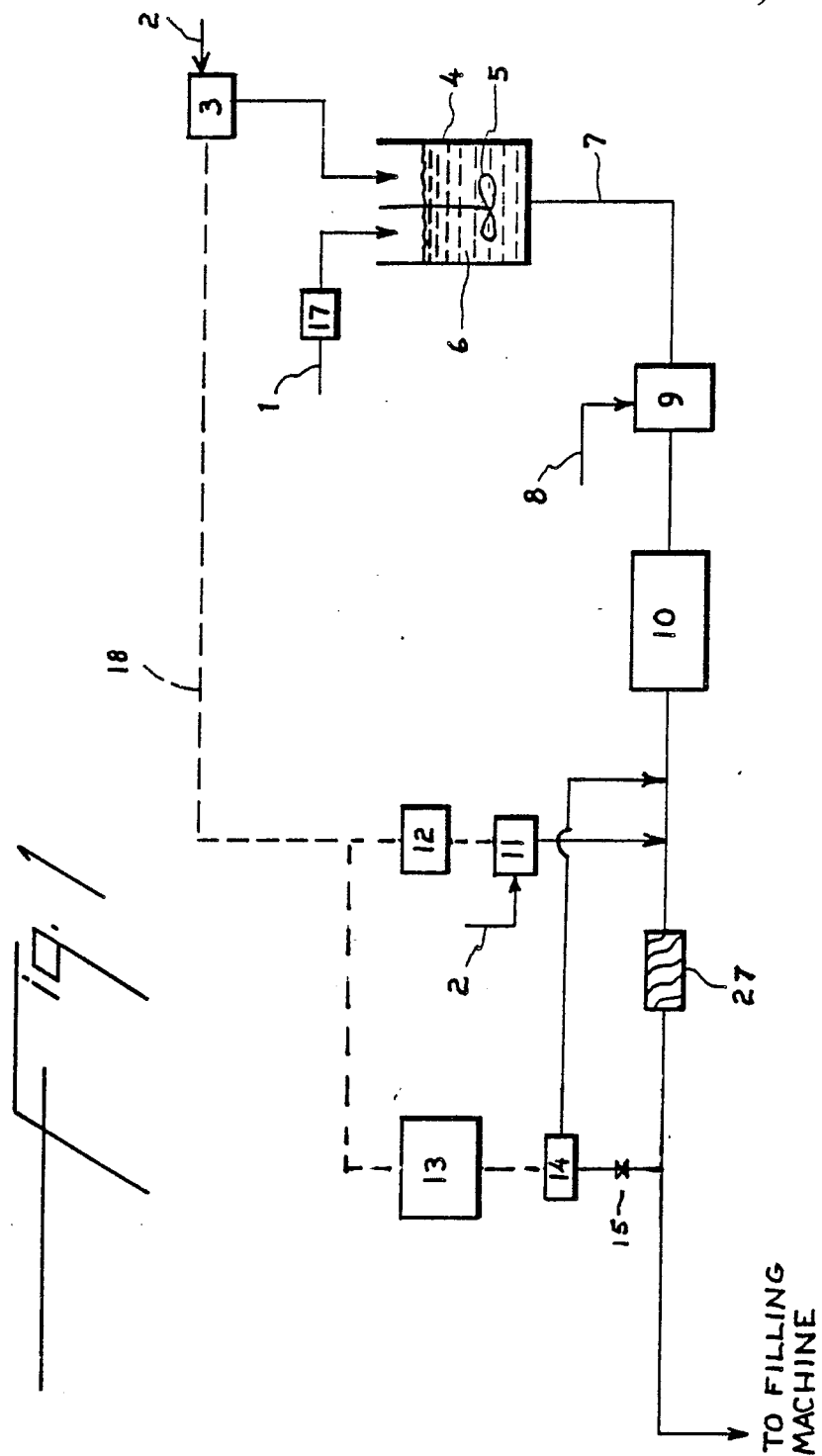
FIG. 1 is a schematic diagram of a typical carbonated beverage mixing and filling process with the beverage analyzer and controller.

FIG. 1 shows a typical beverage mixing and filling line using the beverage analyzer and controller. Syrup is charged into a mixing vessel 4, typically a stainless steel vessel, containing a mixer 5. A metering pump or flow control valve 17 is used to charge the desired amount of syrup 1 into the mixing vessel. Water 2 is charged into the mixing vessel via a metering pump or a flow control valve 3 which can be set and adjusted manually to provide the desired flow. Optionally, the water charged into the mixing vessel can be controlled by the process controller 12, for example, a PLC, programmable logic controller, made by Moore Products Inc. Springhouse, Pa. The water and syrup are mixed to form a beverage 6 and the beverage is passed through stainless steel pipe 7 into the carbonator 9 where $CO_2$ 8 is added to the beverage. The level of carbonation of the beverage is controlled by the pressure of $CO_2$ used which typically is in the range of about 40–70 psig (pounds per square inch gauge). The beverage is then passed into a chiller unit 10 which reduces the temperature of the beverage to about 2°–4° C. The beverage then is passed into a static-in-line mixer 27, for example, a Sata-Tube Motionless Type Mixer made by TAH Industries Inc., Imlaystown, N.J. covered by U.S. Pat. No. 4,093,188. The mixer insures that the beverage is thoroughly mixed before it is filled into containers via a standard filling machine which is not shown. Other conventional static-in-line mixers can be used than the aforementioned type.

A sample of beverage for analysis is removed from the line via valve 15, typically, a pneumatic operated ball valve, and passed into cell 14 for photometric analysis. Preferably, the sample is reintroduced into the process after photometric analysis. The cell 14 is of stainless steel, has quartz windows or another material that transmits U.V. light, a 1 cm path length, uses gaskets of FDA approved EPDM rubber or another type rubber that can be easily sanitized. The cell is of a design that can easily be sanitized and flushed out with water and no portions thereof contain a dead volume of liquid.

The sample of beverage is measured by the photometric analyzer 13 described in U.S. Pat. No. 4,380,586 issued Apr. 19, 1983 to R. S. Saltzman which is hereby incorporated by reference. The photometric analyzer photometrically measures the concentration of syrup in the beverage and generates a signal which is fed to the process controller 12 which compares the syrup concentration of the beverage to a predetermined level of syrup for the standard beverage and then adds a trim amount of water to the beverage so that the syrup concentration is at the desired level.

By the term "trim amount of water" is meant, that small amount of water which is added to the beverage before filling into a container which is sufficient to bring the water and syrup content of the beverage to a predetermined or set standard concentration for that beverage.

In a preferred process, the concentration of syrup in the beverage prepared in the mixing vessel is at a slightly higher level than the standard level and a trim amount of water 2 is added via water control valve 11 to bring the syrup concentration within the standard level. To insure the beverage is thoroughly mixed but with a minimum amount of lag before being sampled and analyzed, it is passed through a static-in-line mixer 27, described above. Static-in-line mixers are not used in conventional mixing and filling processes but are a key component in this invention.

In addition to adding a "trim amount of water", an optional feed back loop 18 can be used to control water being added to the mixing vessel 4. The amount of water can be increased or decreased via control valve 3 which is controlled by the process controller 12.

Figure 2:
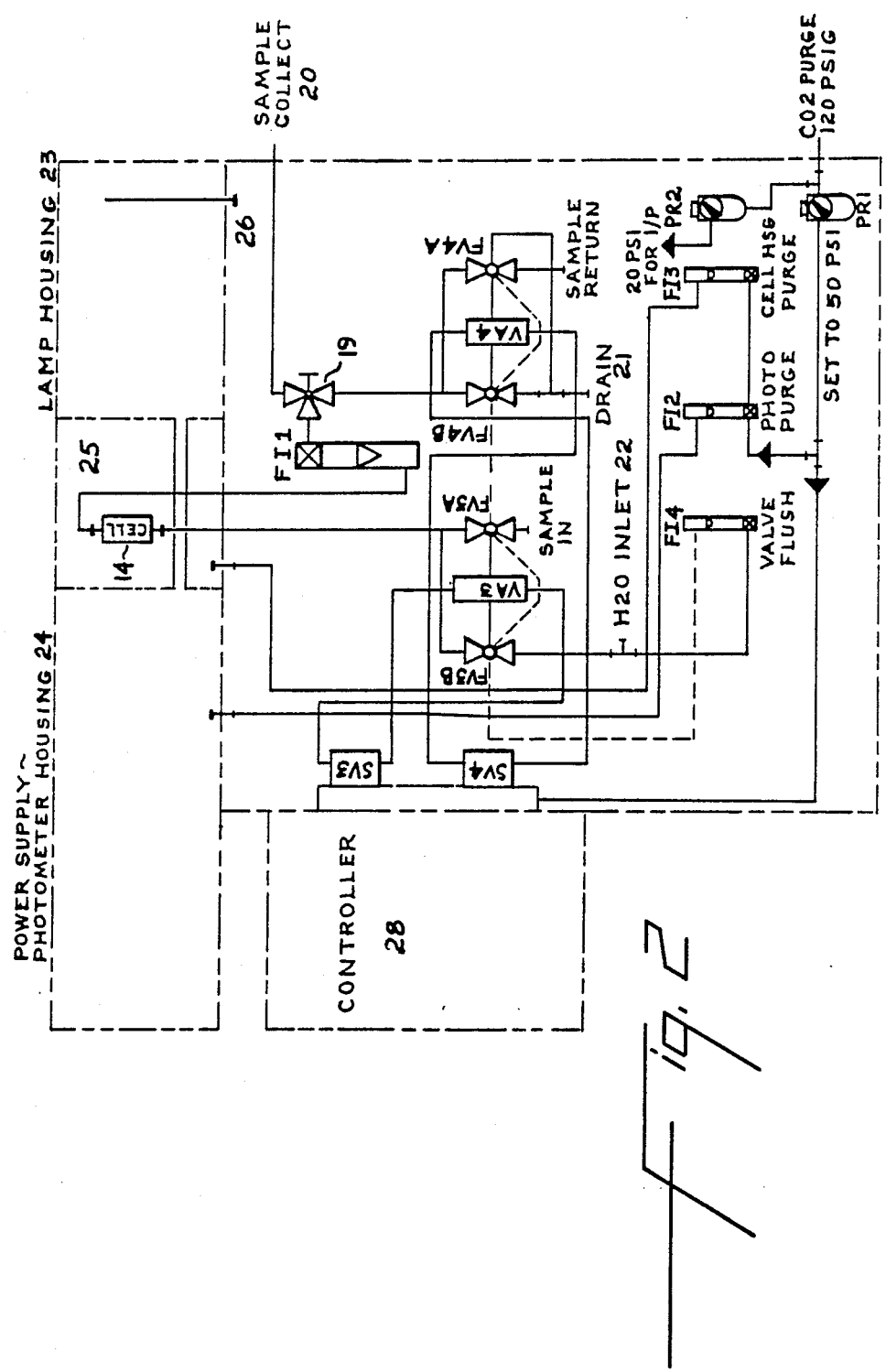
FIG. 2 is a schematic diagram of the beverage analyzer and controller.

The photometric analyzer 13 and the cell 14 are housed together and the valves are mounted together. FIG. 2 shows a schematic diagram of the above. A beverage sample is taken from the line through valve FV3A (shown as valve 15 in FIG. 1) typically, a pneumatically actuated ball valve. The valve is actuated by valve actuator VA3 which is air or $CO_2$ powered. Preferably, $CO_2$ is used since it is clean and dry and readily available in the carbonation step of the process. The sample is passed into cell 14 and after analysis is passed into flow indicator FI1, typically, a rotameter having a range of 100–1600 ml/min. Then the sample is passed through three way valve 19. The sample can be collected via sample collect 20 and sent to a lab for further analysis or the sample can be sent to drain 21 via valve FV4B for disposal or returned to the process via valve FV4A. Both valves FV4A and FV4B are pneumatically actuated ball valves controlled by valve actuator VA4.

When the filling line is not in operation such as occurs when there is a change over of beverages, the cell 14 is flushed out with water. Water enters through an inlet 22 and enters the cell 14 through valve FV3B which is a pneumatically actuated ball valve actuated by valve actuator VA3. As discussed above, the water is passed through flow indicator FI1 and three way valve 19 and sent to drain.

Water is continuously flushed through modified ball valve body cavities (FV3A, FV3B, FV4A and FV4B) to prevent contamination of the beverage. This is accomplished via flow indicator FI4, typically a combination valve assembly of a rotameter and ball valve.

As mentioned above, $CO_2$ is used to actuate the pneumatic valves and also is used to purge components 23, 24 and 25. The purge with dry $CO_2$ prevents condensation of moisture on the outside of windows of cell 14. $CO_2$ enters at a line pressure of 120 psig through pressure regulator PR1 and reduced to 50 psig. Pressure regulator PR1 controls $CO_2$ fed to solenoid valves SV3 and SV4, the purge of the power supply/photometer housing 24 and the cell and lamp housings 23 and 25. Solenoid valves SV3 and SV4 control the pneumatic pressure to valve actuators VA3 and VA4, respectively.

A second pressure regulator PR2 which reduces $CO_2$ pressure to 20 psig is an input to the current to pneumatic (I/P) transducer used to convert the signal from controller 12 to a pneumatic signal to actuate water control valve 11 which typically is a Research Control Valve made by Badger Meter, Inc. Tulsa Okla. Model No. 1002GCN36SVOPCLN36.

$CO_2$ is fed through flow indicator FI2, to purge the power supply/photometer housing 24. The cell and lamp housings 23 and 25 are purged with $CO_2$ through flow indicator FI3. Flow indicators FI2 and FI3 typically are rotameters. $CO_2$ exits the power supply/photometer housing 24 and the cell and lamp housings 23 and 25 through an outlet 26 in the lamp housing 23. The housings are not independently sealed and gas can flow through the housings.

The photometric analyzer is comprised of units 14, 23. 24 and 25 and the basic operation thereof is described in the aforementioned U.S. Pat. No. 4,380,586. The analyzer is a split beam photometric analyzer that uses a metallic discharge mercury vapor lamp, typically a A4/U.V. lamp. The split beam configuration compensates for evolution of small gas bubbles in the sample cell. The reference filter used is a 578 nm (nanometers) filter.

The following are typical filters used for beverage samples:
  436 nm for beverages that use caramel colored syrup such as "Diet Coke", "Pepsi Light", "Dr; Pepper", root beer, cream soda and the like;
  265 nm for beverages such as "7 Up" and "Sprite" and the like:
  289 nm for beverages such as "Regular Slice", "Diet Slice" and gingerale:
  313 nm for beverages such as "Apple Slice", "Mellow Yellow", grape and lemon lime.

For an initial calibration of a given beverage, a standard is prepared with the syrup that is used to prepare the beverage at a desired concentration, and this value is fed and stored in the analyzer controller 28 of the photometric analyzer. The analyzer controller typically is a microprocessor. At the start of a filling run of a given beverage, a sample is collected from the cell and analyzed by a laboratory for syrup content. Based on this laboratory analysis, the calibration of the photometric analyzer is adjusted slightly, typically less than 1% of the preset standard, to match the laboratory analysis. Variations of calibration may result from small changes in syrup flavoring.

An optional method for initially calibrating the photometric analyzer is to use a second cell with a light path length of about 0.15 cm in series with the first cell. The second cell is flushed with water during normal operation and the first cell is flushed with water during the calibration of the photometric analyzer. The second cell after being flushed with water and filled with undiluted syrup is then measured. A calibration is established directly from the syrup reading by extrapolation to the desired beverage level of diluted syrup.

The mercury lamp of the photometric analyzer provides a line source of highly monochromatic and unchanging wavelengths (lines) of U.V. and visible radiation that is highly linear (with Beer's Law) and results in precise readings even at high absorbance levels. Therefore, the photometric analyzer gives a precise analysis, and small differences such as 0.1% can be determined, and the syrup content of the beverage can be controlled to within 0.25-0.50% of a given standard which has been demonstrated on a beverage filling line.

Both the analyzer controller 28 and the process controller 12 have digital readouts so that results can be read directly. Results also can be fed to a recorder and recorded.

The improved process and apparatus of the invention make it possible to precisely control the content of beverages in particular, carbonated sugar-free beverages. With slight modifications in the equipment such as a measuring filter changes, the process and apparatus may be used for controlling the contents of other liquids or beverages.

We claim:

1. In a process for making carbonated beverages in which water is mixed with a syrup in a mixing vessel and the resulting mixture is passed into a carbonator and the beverage is carbonated and a flow stream of the resulting carbonated beverage is passed into a filling machine and filled into containers in a filling line, the improvement used therewith comprises the steps of:
    a. continuously removing sample of beverage from the flow stream after the beverage has been carbonated and before the beverage is filled into containers and then passing the sample of beverage into a cell of a photometric analyzer and photometrically measuring the concentration of syrup in the sample which generates a signal and returning the sample to the flow stream;
    b. feeding the signal to a process controller which compares the signal to a signal stored in the controller that had been generated by the photometric analyzer of an analysis of a sample of a standard beverage containing a predetermined level of syrup concentration and the process controller precisely determines the deviation of syrup concentration of the sample from the standard;
    c. adding a trim amount of water to the flow stream of the beverage after the beverage has left the mixing vessel and has been carbonated to control the syrup concentration of the beverage to the concentration level of the standard, wherein the process controller monitors and controls the trim amount of water being added;
    d. passing the beverage through a static-in-line mixer to provide thorough mixing of the beverage.

2. The process of claim 1 wherein the beverage is passed through a chiller unit before the syrup concentration of the beverage is measured.

3. The process of claim 2 in which the process controller is programmable.

4. The process of claim 1 in which the syrup content of the beverage is controlled within about 0.25-0.50% of the concentration of the standard beverage.

5. The process of claim 1 in which the photometric analyzer is purged with carbon dioxide.

6. A beverage analyzer and controller for use with a carbonated beverage mixing and container filling line in which water is mixed with a syrup in a mixing vessel and the resulting mixture is passed into a carbonator and the beverage is carbonated and a flow stream of the resulting carbonated beverage is passed into a filling machine and filled into containers; wherein the beverage analyzer and controller comprising:
    a. a photometric analyzer containing a sanitizable sample cell which continuously photometrically analyzes the syrup content of a beverage sample flowing through the cell by comparing the absorbance at the sample wave length to that of a reference wave length and generates a signal;
    b. a process controller which receives the signal from the photometric analyzer and compares the signal to a signal stored in the controller having been generated by the photometric analyzer of an analysis of a sample of a standard beverage containing a predetermined level of syrup concentration and precisely determines the deviation of syrup concentration of the sample from the standard;
    c. valve means controlled by the process controller for adding a trim amount of water to the flow stream of the beverage after the beverage has left the mixing vessel and has been carbonated to control the syrup concentration of the beverage to the concentration level of the standard beverage; and
    d. a static-in-line mixer for thoroughly mixing the beverage before analyzing and filling of the beverage into containers.

7. The beverage analyzer and controller of claim 6 in which the photometric analyzer is a split beam photometric analyzer having a UV metallic discharge mercury vapor lamp.

8. The beverage analyzer and controller of claim 7 which uses a reference filter of 578 nm (nanometers) and sample filters of 436 nm, 265 nm, 289 nm and 313 nm.

9. The beverage analyzer and controller of claim 6 having a sanitizable sample cell with quartz windows and an absence of dead volume.

10. The beverage analyzer and controller of claim 6 in which the valving means are pneumatically actuated ball valves actuated by carbon dioxide gas.

11. The beverage analyzer and controller of claim 10 having water flushing means to flush the ball valves when another beverage is being run through the analyzer and controller.

* * * * *